(12) United States Patent
Nabutovsky et al.

(10) Patent No.: US 8,249,707 B2
(45) Date of Patent: Aug. 21, 2012

(54) METHODS AND SYSTEMS FOR IMPROVED ARRHYTHMIA DISCRIMINATION

(75) Inventors: Yelena Nabutovsky, Mountain View, CA (US); Rafael Donnay, Sunnyvale, CA (US); Cecilia Qin Xi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1125 days.

(21) Appl. No.: 12/120,471

(22) Filed: May 14, 2008

(65) Prior Publication Data

US 2009/0287268 A1 Nov. 19, 2009

(51) Int. Cl.
*A61N 1/37* (2006.01)

(52) U.S. Cl. ........................................................ 607/27

(58) Field of Classification Search .......... 600/508–510, 600/515, 518; 607/2–15, 59–63
See application file for complete search history.

(56) References Cited

U.S. PATENT DOCUMENTS

| | | | |
|---|---|---|---|
| 5,421,830 A | 6/1995 | Epstein et al. | |
| 5,509,927 A | 4/1996 | Epstein et al. | |
| 5,697,959 A | 12/1997 | Poore | |
| 6,216,036 B1 * | 4/2001 | Jenkins et al. | 607/27 |
| 6,266,555 B1 | 7/2001 | Werner et al. | |
| 6,694,179 B1 | 2/2004 | Mouchawar et al. | |
| 7,242,978 B2 | 7/2007 | Cao et al. | |
| 7,308,311 B2 | 12/2007 | Sorensen et al. | |
| 7,333,856 B1 | 2/2008 | Er et al. | |
| 2001/0034538 A1 * | 10/2001 | Olson et al. | 607/4 |
| 2005/0137485 A1 | 6/2005 | Cao et al. | |
| 2006/0111643 A1 * | 5/2006 | Cazares et al. | 600/518 |
| 2007/0123788 A1 | 5/2007 | Gunderson et al. | |
| 2007/0123790 A1 | 5/2007 | Gunderson et al. | |
| 2007/0123941 A1 | 5/2007 | Gunderson et al. | |
| 2007/0135863 A1 | 6/2007 | Gunderson et al. | |
| 2007/0135864 A1 | 6/2007 | Gunderson et al. | |
| 2007/0167986 A1 | 7/2007 | Gunderson et al. | |

* cited by examiner

*Primary Examiner* — Carl H Layno
*Assistant Examiner* — Allen Porter, Jr.
(74) *Attorney, Agent, or Firm* — Steven M. Mitchell

(57) ABSTRACT

A non-implanted system receives, from an implantable cardiac device implanted within a patient, data corresponding to detected potential episodes of tachycardia. A representation of the data corresponding to the detected potential episodes of tachycardia is displayed to a user, and the user that observes the displayed representation of the data is allowed to enter a user diagnosis for each of the detected potential episodes of tachycardia. The non-implanted system simulates how the implantable cardiac device can use its discriminators to produce device diagnoses, based on the data for the detected potential episodes of tachycardia, including how adjustments to the discriminators affect how the device diagnoses match the user diagnoses. Thereafter, the non-implanted system can reprogram the implantable cardiac device to increase a likelihood that future device diagnoses produced by the implantable cardiac device would more closely match future user diagnoses produced by the user.

17 Claims, 10 Drawing Sheets

Choose value of discriminator parameter that provides greatest allowance for error Choose value of discriminator parameter that provides greatest allowance for error. If two values have same allowance for error, choose one closest to device default value

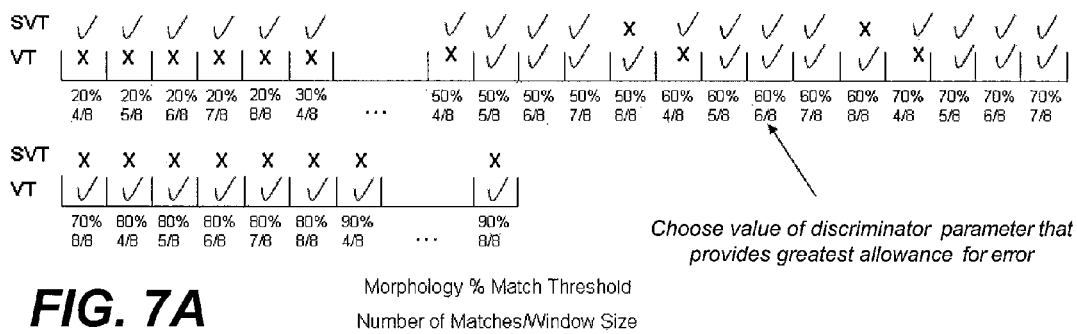

FIG. 7A

Morphology % Match Threshold
Number of Matches/Window Size

Choose value of discriminator parameter that provides greatest allowance for error

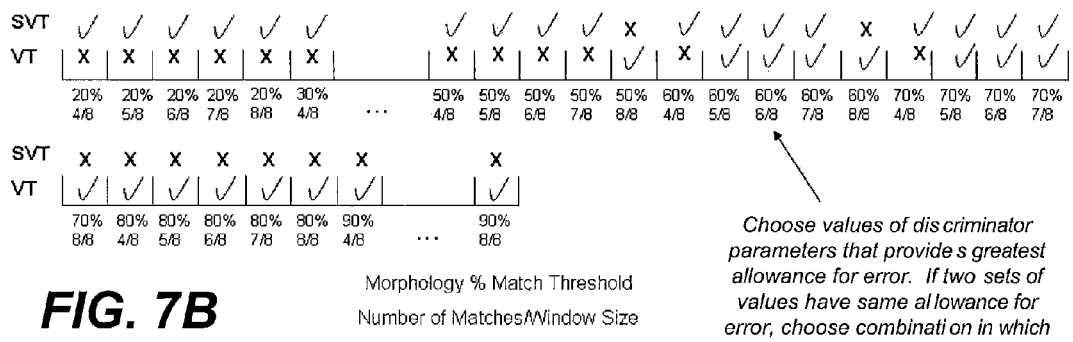

FIG. 7B

Morphology % Match Threshold
Number of Matches/Window Size

Choose values of discriminator parameters that provides greatest allowance for error. If two sets of values have same allowance for error, choose combination in which greatest number of values of discriminator parameters are closest to device default values

METHODS AND SYSTEMS FOR IMPROVED ARRHYTHMIA DISCRIMINATION

FIELD OF THE INVENTION

Embodiments of the present invention relate to implantable cardiac devices, and methods for use therewith, that are used to discriminate between different types of arrhythmias. Embodiments of the present invention also relate to non-implanted systems, which may include programmers, that are used to program and reprogram such implantable cardiac devices.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Arrhythmias that result in a heart rate slower than normal are called bradyarrhythmias, which are also known as bradycardias. Arrhythmias that result in a faster heart rate than normal are called tachyarrhythmias, which are also known as tachycardias. Tachycardias are further classified as supraventricular or ventricular. Supraventricular tachycardias (SVTS) are characterized by abnormal rhythms that may originate in the atria, the atrioventricular node (AV node), or in the pulmonary veins. For example, a paroxysmal SVT can exhibit heart rates between approximately 140 beats per minute (bpm) and approximately 250 bpm. However, the most common SVTs are typically atrial flutter (AFl) and atrial fibrillation (AF). In addition, many SVTs involve the AV node, for example, AV nodal reentry tachycardia (AVNRT) where an electrical loop or circuit includes the AV node.

Atrial flutter (AFl) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are typically not immediately life threatening when compared to ventricular arrhythmias, examples of which are discussed below. SVTs can typically be left untreated for long periods of time without significant harm to the patient.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of 100 bpm or more. Such activity may degenerate further into disorganized electrical activity, known as VF. In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia.

VF is typically fatal if not terminated within minutes using shock therapy. VT can be lethal if not treated promptly, and is usually treated using either anti-tachycardia pacing (ATP) or shock therapy to terminate an episode of VT.

It has been common practice for an implantable cardioverter defibrillator (ICD) to monitor heart rate, or more commonly the ventricular rate, of a patient and classify the cardiac condition of the patient based on this heart rate. For example, a tachyarrhythmia may be defined as any rate in a range above a designated threshold. This range is then divided into ventricular tachycardia and ventricular fibrillation zones. The ventricular tachycardia zone may be further divided into slow ventricular tachycardia and fast ventricular tachycardia zones.

As described above, SVTs and ventricular arrhythmias may lead to ventricular rates in excess of 100 bpm. In other words, ventricular rates of SVTs can overlap with rates of tachycardias of ventricular origin. These SVTs are often well tolerated and require no intervention. Further, physically active patients can have heart rates during exercise that overlap with their tachycardia rates. Accordingly, discrimination of VT from SVT may require more than just knowledge of a patient's ventricular rate. In other words, using heart rate as the sole criterion to diagnose the cardiac condition of a patient is often not sufficient.

To improve device diagnoses, many implantable cardiac devices can also examine the morphology of an intracardiac electrogram (EGM) and/or electrocardiogram (ECG), in addition to the heart rate. The shape of an intracardiac complex can include information on the origin and sequence of the heart's electrical activity. A normal intracardiac complex traverses the AV node and is conducted by specialized cardiac tissue throughout the ventricles. This results in a distinctive complex morphology. A tachycardia of ventricular origin often has a different morphology due to its ectopic origin and conductance through cardiac muscle tissue. As such, in addition to monitoring heart rate, some implantable cardiac devices are capable of performing morphology discrimination to classify the cardiac condition of the patient (i.e., to produce a device diagnosis). For example, a template based on the morphology of a "known" signal can be stored in the implantable cardiac device. The "known" signal can be, for example, a signal collected during a period where a patient is known to exhibit a normal sinus rhythm. By comparing the morphology characteristics (e.g., number, amplitude, sequence and/or polarity of waveform peaks, as well as the area under the peaks) of an arrhythmia to the template, the implantable cardiac device can calculate the match between the waveforms. For a further description of morphology discrimination, refer to U.S. Pat. No. 5,240,009 (Williams), entitled "Medical Device with Morphology Discrimination" and to U.S. Pat. No. 5,779,645 (Olson et al.), entitled "System and Method for Waveform Morphology Comparison," which patents are hereby incorporated by reference. For more specific examples, a morphology percentage match threshold and/or a number of matches in a given window can be defined. These are just a few examples of morphology discriminators, which are not intended to be limiting.

Sudden onset and interval stability (also know as rate stability), which are discussed in more detail below, are examples of other factors that can be monitored to improve device diagnoses. Also, the relationship between ventricular rate (V) and atrial rate (A) can be used. For example, this can be part of a rate branch algorithm, which, depending on V and A, may follow one of three branches: a V<A rate branch; a V=A (within a specified tolerance) rate branch; and a V>A rate branch. If V<A, then morphology discrimination and/or interval stability may be available to distinguish VT from AF or AFI. If A and V are essentially the same (within a certain tolerance), then morphology discrimination and/or sudden onset may be available to distinguish VT from sinus tachycardia. If V>A, then an arrhythmia may be characterized as VT. Also, specific branches can be turned on or off. For example, if V is greater than the tachycardia threshold but essentially the same as A, and the V=A branch is turned off, then the algorithm can cause the V>A branch to be followed, and the arrhythmia may be classified as VT. Additional details of an exemplary rate branch algorithm are provided in U.S. Pat. No. 6,636,764 (Fain et al.), entitled "Safety Backup in Arrhythmia Discrimination Algorithm," which is incorporated herein by reference. Atrioventricular association (AVA) can also be used to distinguish AFI from VT. In an exemplary (AVA) algorithm, the AV interval is measured from each ventricular sensed event to its preceding atrial event and an AVA Delta is then calculated as the difference between the second longest AV interval and the second shortest AV interval in a recent group of intervals. If the measured AVA Delta is less than a programmable AVA threshold parameter, the AV intervals are considered stable, which is indicative of SVT. If the measured AVA Delta is greater than or equal to a programmable AVA threshold parameter, the AV intervals are considered unstable, which is indicative of VT. More generally, discriminators relating to the relative rate of the atria and ventricles and/or the timing relationship between atrial and ventricular events can be used to produce device diagnoses.

An implantable cardiac device can be programmed to provide a therapy in response to an arrhythmia being detected, where the type of therapy corresponds to the type of arrhythmia that the device believes it has detected (the arrhythmia the device believes it has detected can be referred to as the device diagnosis). For example, VT may be treated with a therapy consisting of low-energy pacing pulses designed to capture the ventricles. This therapy is referred to as Anti-Tachycardia Pacing therapy (ATP). VT may also be treated with relatively low energy, synchronized cardioversion shocks. VF, on the other hand, is typically treated more aggressively with high energy shocks. The implantable cardiac device is programmed with numerous parameters that are used to discriminate between types of arrhythmias, and to define the types of therapies to be used to treat the various arrhythmias. An SVT may or may not be treated, depending on how the implantable cardiac device is programmed.

Over the years, the number of programmable arrhythmia discriminators has increased. A major challenge for both implantable cardiac device manufacturers and caregivers (e.g., physicians, clinicians, and the like) is to select proper uses of these discriminators and values of parameters of theses discriminators. While a manufacturer may provide nominal values of parameters and uses of these discriminators, these nominal values and uses (also referred to as default values and uses) may not be proper for all patients, and it is up to the caregiver to change them, e.g., using statistical information, knowledge of the patient and his/her condition, and the caregiver's personal experience.

Caregivers often have difficulty programming discriminators intended to aid in the discrimination of tachycardias (e.g., SVT from VT), because the implications of making adjustments to discriminators are often not readily clear. As a result, caregivers often do not turn on certain discriminators routinely, waiting to see if the patient will receive inappropriate therapies before attempting to reprogram the device appropriately, or caregivers turn the discriminators on with the default parameter values provided by the manufacturer, without any attempt to customize them for the individual needs of the patient.

As can be appreciated from the above description, implantable cardiac devices face the difficult challenge of appropriately discriminating between different types of arrhythmias, such as VT and SVT. Several discrimination algorithms exist that rely on discriminators to differentiate such arrhythmias. However, appropriate programming of these algorithms, including the appropriate selection of parameter values and uses of specific discriminators, can be challenging due to algorithm complexity, patient to patient variability, change in patient condition, and lack of information available to the caregiver at the time of the device implant. Accordingly, there is still a need to assist physicians, clinicians and other caregivers (generally referred to as users) in programming discriminators in a way more appropriate to the indications and characteristics of individual patients. More generally, there is still a need to improve how implantable cardiac devices are programmed to perform arrhythmia discrimination.

SUMMARY

Embodiments of the present invention relate to systems and methods that can be used to improve arrhythmia discrimination, e.g., between different types of tachycardias, such as, but not limited to, VT and SVT.

Specific embodiments of the present invention are for use by a non-implanted system configured to communicate with implantable cardiac devices implanted within patients. Such implantable cardiac devices can be configured to detect potential episodes of tachycardia and to store data corresponding to the detected potential episodes of tachycardia. Additionally, such implantable cardiac device can have programmable arrhythmia discriminators that are used to discriminate between different types of tachycardia, e.g., VT and SVT.

In accordance with an embodiment, a non-implanted system receives, from an implantable cardiac device implanted within the patient, data corresponding to detected potential episodes of tachycardia. A representation of the data corresponding to the detected potential episodes of tachycardia is displayed to a user (e.g., a physician, clinician or other caregiver), and the user that observes the displayed representation of the data is allowed to enter a user diagnosis for each of the detected potential episodes of tachycardia. This can include displaying EGM and/or ECG waveforms corresponding to the detected potential episodes of tachycardia, as well as alpha-numeric attribute information about the displayed EGM and/or ECG waveforms, and/or a representation of physiologic data (corresponding to detected potential episodes of tachycardia) obtained using one or more implanted physiologic sensor.

In accordance with an embodiment, the non-implanted system simulates how the implantable cardiac device would use its discriminators to produce device diagnoses, based on the data for the detected potential episodes of tachycardia, including how adjustments to the discriminators affect how the device diagnoses match the user diagnoses. In accordance with an embodiment, the non-implanted system automatically adjusts one or more of the discriminators to thereby cause the simulated device diagnoses to more closely match that user diagnoses. This can include automatically adjusting one or more of the discriminators until the simulated device diagnoses match the user diagnoses to within a specified tolerance.

Thereafter, the non-implanted system can reprogram the implantable cardiac device by sending instructions to the implantable cardiac device, specifying adjustments to the discriminators that increase a likelihood that future device diagnoses produced by the implantable device would more closely match future user diagnoses produced by the user. Such adjustments can relate to settings such as which discriminators are used, when discriminators are used, an order in which discriminators are used, how discriminators are used, how many discriminators must be satisfied for a rhythm to be characterized as a specific type of tachycardia and/or values of parameters of discriminators.

In accordance with an embodiment, if more than one setting for one of the discriminators results in the same match between the simulated device diagnosis and the user diagnosis, then the setting that provides the greatest allowance for error is selected. Where settings result in the same match between the simulated device diagnosis and the user diagnosis and result in the same allowance for error, then the setting that is the closest to the default setting can be selected. Alternatively, when more than one setting for one of the discriminators results in the same match between the simulated device diagnosis and the user diagnosis, then the setting that is the closest to the default setting can be the one that is initially selected. In still another embodiment, if more than one setting for one of the discriminators results in the same match between the simulated device diagnosis and the user diagnosis, the setting that is the same as or closest to the current setting of the implantable cardiac device is selected.

This summary is not intended to be a complete description of the invention. Other features and advantages of the invention will appear from the following description in which the preferred embodiments have been set forth in detail, in conjunction with the accompanying drawings and claims.

BRIEF DESCRIPTION OF THE DRAWINGS

FIGS. 7A and 7B are used to describe how embodiments of the present invention can be used to select values for two discriminator parameters that are used to discriminate between SVT and VT.

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods, which are for use in discriminating between different types of arrhythmias, are generally intended for use with an implantable cardiac device capable of detecting and treating arrhythmias, and with a non-implanted system that can communicate with such an implantable cardiac device (e.g., to upload information from the implantable cardiac device and/or reprogram the implantable cardiac device). An exemplary implantable cardiac device will thus be described in conjunction with FIGS. 1 and 2. Additionally, FIGS. 3A and 3B will be used to describe an exemplary external programmer that can be used to program implantable cardiac devices, as well as upload information from implantable cardiac devices and analyze such information. It is recognized, however, that numerous variations of such devices exist, and the embodiments of the present invention are not limited to use with the exemplary devices described.

Exemplary Implantable Cardiac Stimulation Device

Figure 1:
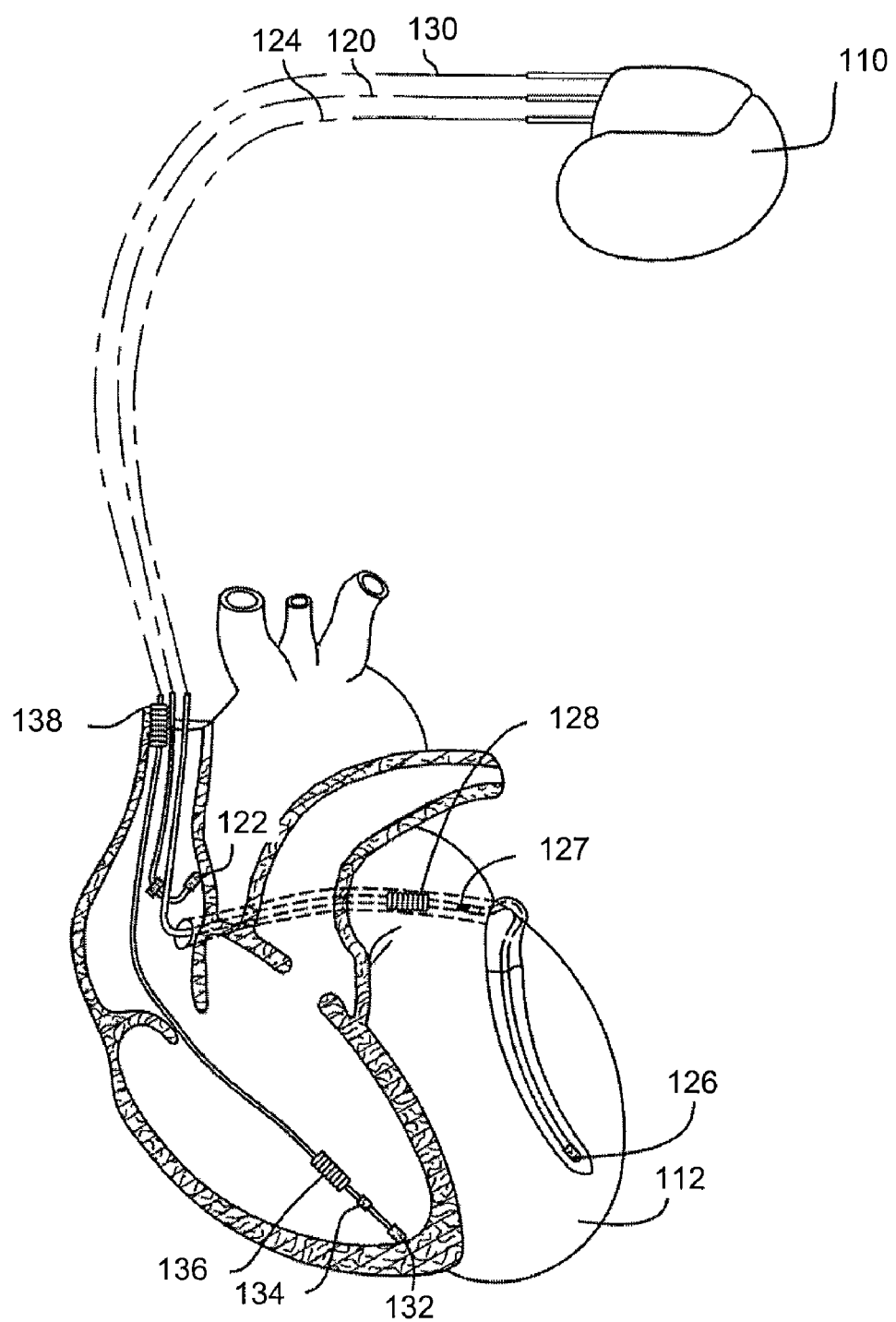
FIG. 1 is a simplified, partly cutaway view illustrating an implantable stimulation device in electrical communication with at least three leads implanted into a patient's heart for delivering multi-chamber stimulation and shock therapy and sensing cardiac activity.

Referring to FIG. 1, an exemplary implantable device 110 (also referred to as a pacing device, a pacing apparatus, a cardiac stimulation device, or simply a device) is in electrical communication with a patient's heart 112 by way of three leads, 120, 124 and 130, suitable for delivering multi-chamber stimulation. Preferably, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
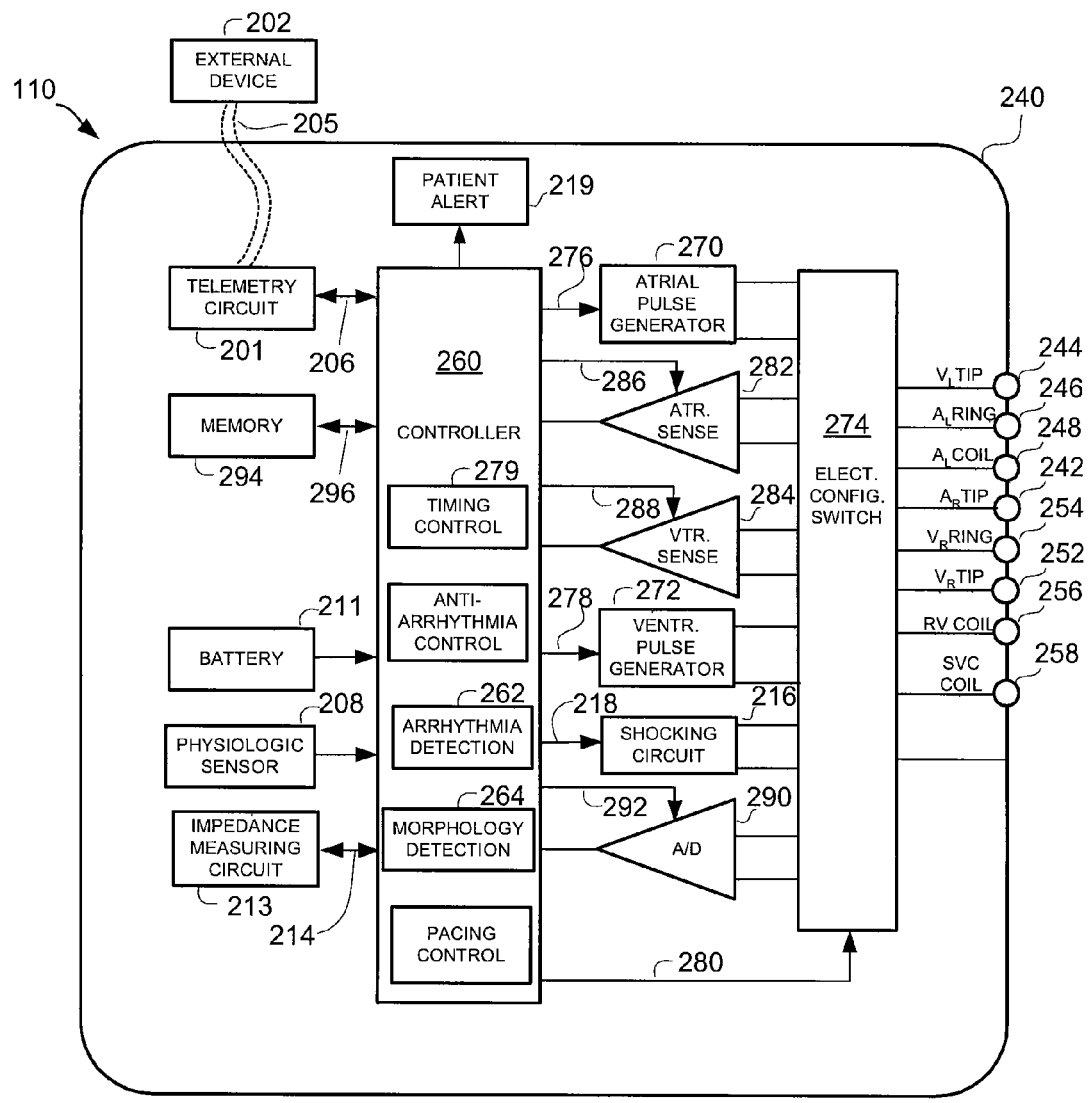
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal (AR TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 26Q are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 includes an arrhythmia detector 262 and a morphology detector 264, that utilizes the atrial and ventricular sensing circuits, 282 and 284, to sense cardiac signals to determine whether a rhythm is physiologic or pathologic. The morphology detector 264 can, e.g., assess characteristics such as amplitude, area under curves, polarity, and shape, of detected cardiac rhythms.

The arrhythmia detector 264 can analyze the timing intervals between sensed events (e.g., P-waves, R-waves, and depolarization signals associated with fibrillation) and compare them to predefined rate zone limits (e.g., bradycardia, normal, low rate VT, high rate VT, and fibrillation rate zones), and analyze various other characteristics such as morphology (as determined by the morphology detector 264), sudden onset, stability, data from physiologic sensors, etc., in order to classify an arrhythmia, and thus, determine the type of remedial therapy that may be needed (e.g., bradycardia pacing, anti-tachycardia pacing, cardioversion shocks or defibrillation shocks).

The arrhythmia detector 262 and/or morphology detector 264 can be implemented within the microcontroller 260, as shown in FIG. 2. Thus, the detectors 262 and/or 264 can be implemented by software, firmware, or combinations thereof. It is also possible that all, or portions, of the arrhythmia detector 262 and/or morphology detector 264 can be implemented using hardware. Further, it is also possible that all, or portions, of the detectors 262 and/or 264 can be implemented separate from the microcontroller 260. It is also possible that the features of the arrhythmia detector and morphology detector be incorporated into a single detector. These detectors can execute arrhythmia discrimination algorithms that use discriminators to assist in classifying arrhythmias. Values of parameters of such discriminators and uses of such discriminators can be adjusted in accordance with embodiments of the present invention, as described below.

Exemplary types of arrhythmias that the arrhythmia detector 262 can detect include, but are not limited to, SVT (e.g., AF), VT and VF. As mentioned above, a tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). VTs begins in the ventricles. Some are harmless, but others are life threatening in that they can quickly deteriorate to VF. Some VTs are harmful even before they deteriorate into VF, or even if they don't deteriorate to VF (e.g., they can cause hemodynamic deterioration that can cause collapse).

VF is a very fast (e.g., over 200 beats per minute) and chaotic heart rate in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF typically quickly becomes more erratic, often resulting in sudden cardiac arrest. This arrhythmia should be corrected immediately via a shock from an external defibrillator or an implantable cardioverter defibrillator (ICD). The defibrillator stops the chaotic electrical activity and restores normal heart rhythm. These are just a few examples of the types of arrhythmias that the arrhythmia detector 262 can detect. One of ordinary skill in the art will appreciate that other types of arrhythmias can be detected, and information for such other types of arrhythmias can be stored.

Still referring to FIG. 2, cardiac signals are also applied to the inputs of an analog-to-digital (A/D) data acquisition system 290. The data acquisition system 290 is configured to acquire intracardiac electrogram (EGM) signals, convert the raw analog data into a digital signal, and store the digital signals or portions thereof for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes. In specific embodiments, the data acquisition system 290 may be used to acquire EGM signals for the analysis, and to store data indicative of portions of such signals in the memory 294.

In accordance with embodiments of the present invention, the implantable device 110 can store, in memory 294, EGM data corresponding to the period immediately prior to, during and subsequent to a detected arrhythmia. The implantable device can also store data that identifies the type of arrhythmia (as diagnosed by the device), the time of the arrhythmia (e.g., a time stamp), the duration of the arrhythmia, as well as any other type of information that a caregiver may deem useful. U.S. Pat. No. 4,295,474 (Fischell) and U.S. Pat. No. 5,732,708 (Nau et al.), each of which is incorporated herein by reference, provide exemplary additional details of the types of data that can be stored in response to the detection of an arrhythmia (and other cardiac events), and how such data can be efficiently and effectively stored.

Where the implantable system include extracardiac subcutaneous electrodes, the sensing circuits can be used to acquire ECG signals, and the data acquisition system 290 may be used to acquire ECG signal data for the analysis, and to store data indicative of portions of ECG signals in the memory 294. Additional details of an exemplary implantable system including extracardiac subcutaneous electrodes are described in U.S. patent application Ser. No. 10/998,026, entitled "Systems and Methods for Detection of VT and VF from Remote Sensing Electrodes," filed Nov. 24, 2004, which is incorporated herein by reference.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also store information about discriminator settings including, but not limited to, information about which discriminators are used, when discriminators are used, an order in which discriminators are used, how discriminators are used, how many discriminators must be satisfied for a rhythm to be characterized as a specific type of tachycardia, and values of parameters of discriminators (also referred to as discriminator parameters).

The implantable device can also include one or more physiologic sensor 208, which can be a "rate-responsive" sensor used to adjust pacing stimulation rate according to the exercise state of the patient. Additionally, or alternatively, the physiological sensor 208 may further be used to detect changes in cardiac output, changes in the physiological condition of the heart, or diurnal changes in activity (e.g., detecting sleep and wake states). While shown in FIG. 2 as being included within the device 110, it is to be understood that one or more physiologic sensor 208 may also be external to the stimulation device 110 and may include a variety of sensors 208 some or all of which may be external to the device 110, yet still be implanted within or carried by the patient. It should also be understood that the communication between the sensor 208 and the device 110 can include wired or wireless communication in various embodiments. A common type of rate responsive sensor is an activity sensor, such as an accelerometer or a piezoelectric crystal, which is mounted within the housing 240 of the device 110. Other types of physiologic sensors 208 are also known, for example, sensors which sense respiration rate and/or tidal volume, arterial and/or venous $O_2$ saturation, heart stroke volume, stroke impedance, ventricular and/or atrial pressure, temperature, patient orientation and/or movement, hemodynamic status, minute ventilation, pH of blood, ventricular gradient, etc.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

The operating parameters of the implantable device 110, including arrhythmia discriminator uses and discriminator parameter values, may be non-invasively programmed into the memory 294 through a telemetry circuit 201 in telemetric communication via communication link 205 with an external device 202, such as a programmer, transtelephonic transceiver, and/or a diagnostic system analyzer. The telemetry circuit 201 can be activated by the microcontroller 260 by a control signal 206. The telemetry circuit 201 advantageously allows EGM and/or ECG signal data, data collected by sensor(s) 208, and status information relating to the operation of the device 110 (as contained in the microcontroller 260 or memory 294) to be sent to the external device 202 through an established communication link 205. In specific embodiments of the present invention, EGM and/or ECG signal data and/or data collected by sensor(s) 208, which correspond to detected potential episodes of an arrhythmia (e.g., tachycardia), are sent to the external device 202 through the established communication link 205. Information about default and/or currently programmed settings for discriminator uses and parameter values can also be transferred from the implantable device 110 to the external device 202 via the communications link 205.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected. Certain embodiments of the present invention, as will be appreciated from the discussion further below, can be used to extend the life a the battery 211 by reducing the quantity of high voltage shocks delivered.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

Because the implantable device 110 may operate as an implantable cardioverter defibrillator device, it should detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode). Use of additional and/or alternative electrodes is also possible, as would be appreciated by one of ordinary skill in the art.

The above described implantable device 110 was described as an exemplary device. One or ordinary skill in the art would understand that embodiments of the present invention can be used with alternative types of implantable devices. Accordingly, embodiments of the present invention should not be limited to use only with the above described device.

Exemplary External Programmer

Figure 3A:
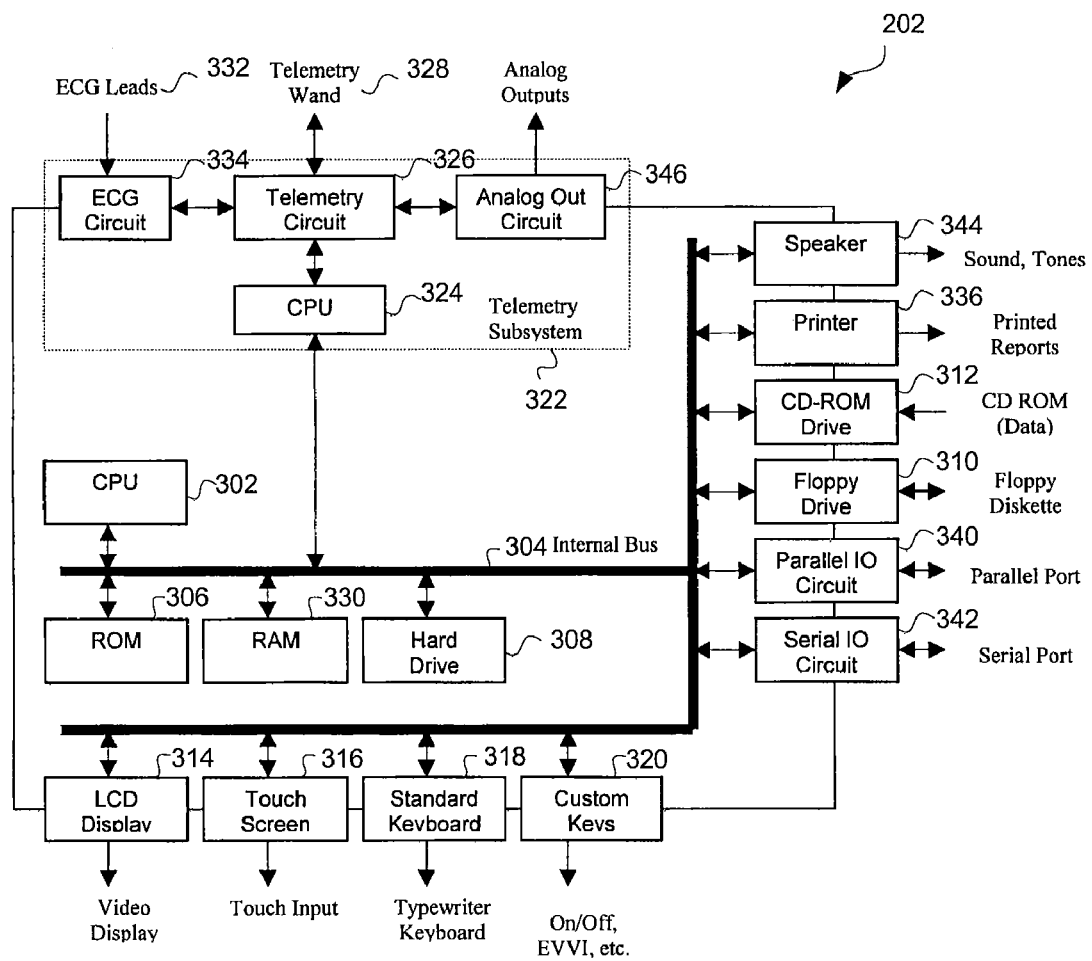
FIG. 3A is a functional block diagram of an exemplary external programmer device that can be used to program the implantable device of FIGS. 1 and 2, and to upload and analyze data collected by the implantable device.

FIG. 3A will now be used to illustrate components of an exemplary external programmer 202 for use in programming the implantable device 110, uploading data from the implantable device, and analyzing such data. Briefly, the programmer permits a physician or other caregiver (also referred to as user) to program the operation of the implantable device 110 and to retrieve and display information received from the implantable device such as EGM and/or ECG data and device diagnostic data. Additionally, the external programmer can receive and display EKG data from separate external EKG leads that may be attached to the patient. As will be described in further detail below, in accordance with embodiments of the present invention, the external programmer 202 is capable of processing and analyzing data received from the implantable device 110.

Operations of the programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU 302 displays a menu of programming options to the user via an LCD display 314 or other suitable computer display device. To this end, the CPU may, for example, display a menu of specific programming parameters of the implantable device to be programmed or may display a menu of types of diagnostic data to be retrieved and displayed. In response thereto, the caregiver enters various commands via either a touch screen 316 overlaid on the LCD display or through a standard keyboard 318 supplemented by additional custom keys 320, such as an emergency VVI (EVVI) key. The EVVI key sets the implantable device to a safe VVI mode with high pacing outputs. This ensures life sustaining pacing operation in nearly all situations but by no means is it desirable to leave the implantable device in the EVVI mode at all times. These are just a few examples of the types of user interfaces of the programmer, which are not meant to be limiting. Inclusion and use of other types of user interfaces are possible, and within the scope of the present invention.

Once all pacing leads are mounted and the implantable device 110 is implanted, the various devices are programmed. Typically, the caregiver initially controls the programmer 202 to retrieve data stored within any implantable device 110 and to also retrieve EKG data from EKG leads 332, if any, coupled to the patient. To this end, the CPU 302 transmits appropriate signals to a telemetry subsystem 322, which provides components for directly interfacing with the implantable device 110, and the EKG leads. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to telemetry wand 328, which, in turn, receives and transmits signals electromagnetically from the telemetry unit 201 of the implantable device 110. The telemetry wand 328 is placed over the chest of the patient near the implantable device to permit reliable transmission of data between the telemetry wand 328 and the implantable device 110.

Typically, at the beginning of the programming session, the external programming device 202 controls the implantable device 110 via appropriate signals generated by the telemetry wand 328 to output previously recorded patient and device diagnostic information. Patient diagnostic information includes, for example, recorded EGM and/or ECG data and statistical patient data such as the percentage of paced versus sensed heartbeats. Device diagnostic data includes, for example, information representative of the operation of the implantable device such as lead impedances, battery voltages, battery recommended replacement time (RRT) information and the like. Data retrieved from the implantable device 110 is stored by external programmer 202, e.g., within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once the patient and device diagnostic data previously stored within the implantable device 110 is transferred to programmer 202, the implantable device 110 may be further controlled to transmit additional data in real time as it is detected by the implantable device 110, such as additional EGM and/or ECG data, lead impedance data, and the like.

As will be explained in more detail below, in specific embodiments of the present invention the programmer 202, the programmer can be used to adjust the uses and/or parameter values of discriminators that the device 110 uses to discriminate between different tachycardias (VT and SVT). More specifically, the telemetry subsystem 322 can be used to make such adjustments to the discriminators of the implantable device 110, as will be described in more detail below.

It is also possible that the telemetry subsystem 322 receives EKG signals from EKG leads 332 via an EKG processing circuit 334. As with data retrieved from the implantable device itself, signals received from the EKG leads can be stored within one or more of the storage devices of the external programmer. Typically, EKG leads output analog electrical signals representative of the EKG. Accordingly, EKG circuit 334 includes analog to digital conversion circuitry for converting the signals to digital data appropriate for further processing within programmer. Depending upon the implementation, the EKG circuit 334 may be configured to convert the analog signals into event record data for ease of processing along with the event record data retrieved from the implantable device. Typically, signals received from the EKG leads are received and processed in real time. Thus, the programmer 202 can receive data both from the implantable device 110 and from the external EKG leads 332.

Data retrieved from the implantable device 110 includes parameters representative of the current programming state of the implantable device 110. Under the control of the caregiver, the external programmer 202 can display the current programming parameters and permits the caregiver to reprogram the parameters. To this end, the caregiver enters appropriate commands via any of the aforementioned input devices and, under control of CPU) 302, the programming commands are converted to specific programming parameters for transmission to the implantable device 110 via telemetry wand 328 to thereby reprogram the implantable device 110. A wide variety of parameters may be programmed by the caregiver, including, but not limited to atrioventricular and inter-ventricular delay values. As mentioned above, programmable parameters also include uses and parameter values of discriminators that can be used to discriminate between different types of arrhythmias. Prior to reprogramming specific parameters, the caregiver may control the external programmer 202 to display any or all of the data retrieved from the implantable device 110 or from the EKG leads, including displays of ECGs, EGMs, and statistical patient information. Any or all of the information displayed by programmer may also be printed using a printer 336.

The programmer 202 can also include a modem (not shown) to permit direct transmission of data to other programmers via the public switched telephone network (PSTN) or other interconnection line, such as a T1 line or fiber optic cable. Depending upon the implementation, the modem may be connected directly to internal bus 304 may be connected to the internal bus via either a parallel port 340 or a serial port 342. Other peripheral devices may be connected to the external programmer via parallel port 340 or a serial port 342 as well. Although one of each is shown, a plurality of input output (IO) ports might be provided. A speaker 344 is included for providing audible tones to the user, such as a warning beep in the event improper input is provided by the caregiver. The telemetry subsystem 322 additionally includes an analog output circuit 346 for controlling the transmission of analog output signals, such as EGM signals output to an EKG machine or chart recorder.

With the programmer 202 configured as shown, a physician or other caregiver operating the external programmer 202 is capable of retrieving, processing and displaying a wide range of information received from the implantable device 110 (and from the EKG leads) initially program and/or to reprogram the implantable device 110 if needed. The descriptions provided herein with respect to FIG. 3A are intended merely to provide an overview of the operation of an exemplary external programmer 202 and are not intended to describe in detail every feature of the hardware and software of the device and is not intended to provide an exhaustive list of the functions performed by the device.

Figure 3B:
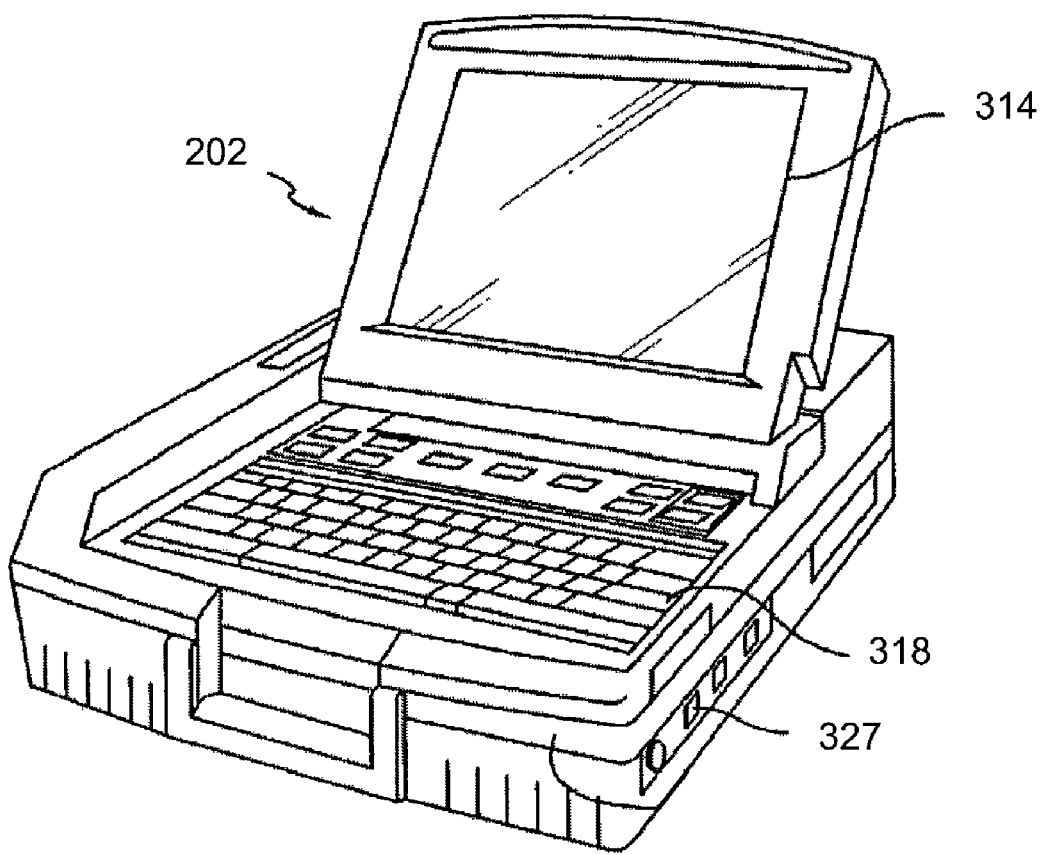
FIG. 3B is an exemplary perspective view of the exemplary external programmer device of FIG. 3A.

FIG. 3B is an exemplary perspective view of the exemplary programmer 202 introduced in FIG. 3A. Referring to FIG. 3B, the programmer 202 is shown as including a display 314, a keyboard 318, and a connector 327 for accepting a cable of a telemetry wand (328 in FIG. 3A).

A programmer similar to programmer 202 can be used to perform many of the features of the present invention described below. It is also possible that a programmer is part of a larger non-implanted system. For example, a general purpose computer system in communications with a programmer can perform some of the processing used to implement features (e.g., simulations) of the present invention.

Specific Embodiments of the Present Invention

Figure 4:
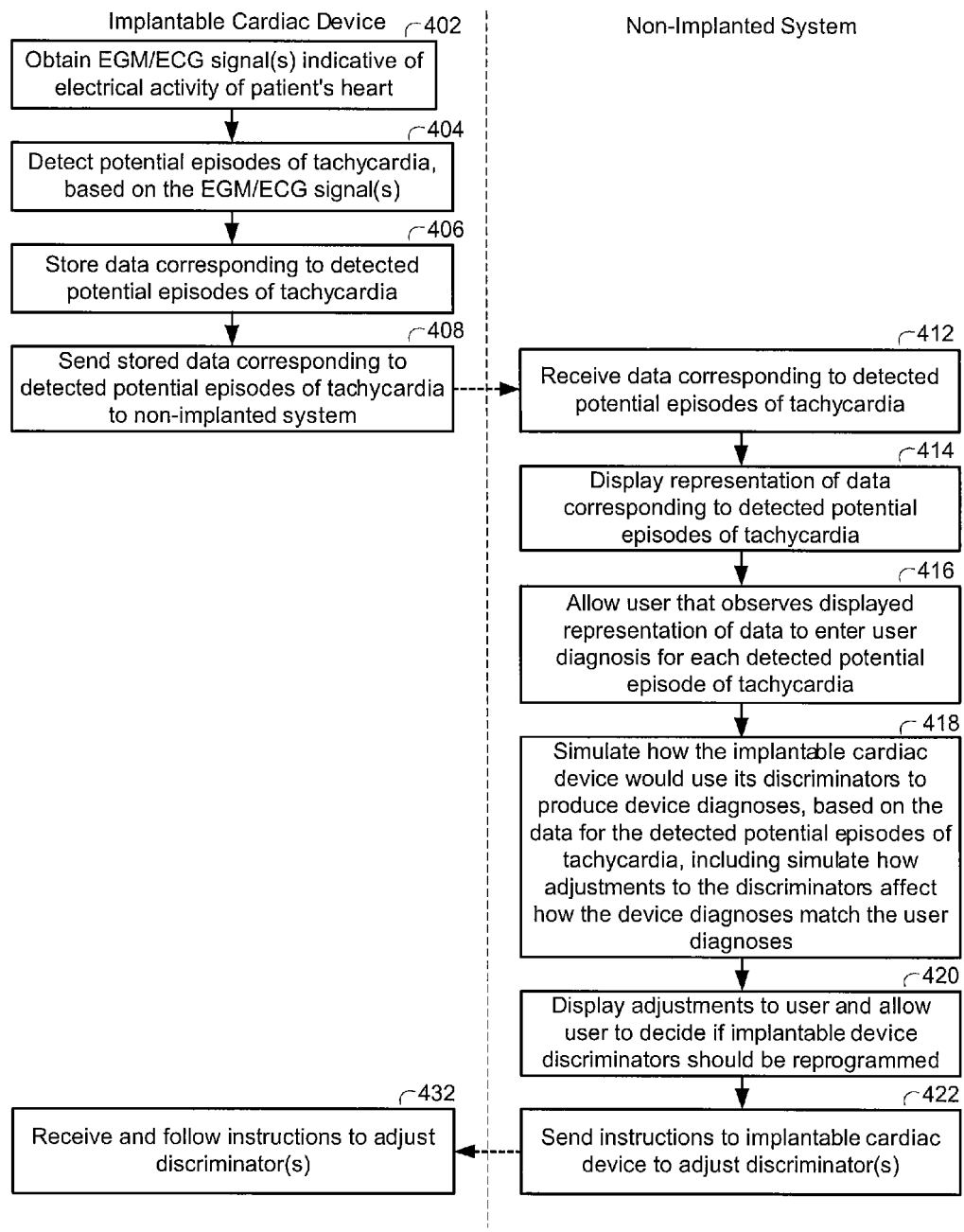
FIG. 4 is a high level flow diagram that is used to summarize specific embodiments of the present invention.

FIG. 4 is a high level flow diagram that is used to describe various embodiments of the present invention. Referring to FIG. 4, the steps shown on the left are performed by an implantable cardiac device (e.g., similar to device 110), and the steps shown on the right are performed by a non-implanted system, which may include a programmer (e.g., similar to the programmer 202). Many existing implantable cardiac devices, including those that have already been employed "in the field", are already programmed to perform steps 402-408. In contrast, the steps on the right are novel and are the focus of many embodiments of the present invention. Nevertheless, to provide a better understanding of the embodiments of the present invention, it is useful to also describe some of the preliminary steps (e.g., 402-408) that are performed by an implantable cardiac device. Further, it can be appreciated from FIG. 4 and the above and below explanations of FIG. 4 that embodiments of the present invention can be used to improve how already implanted cardiac devices perform arrhythmia discrimination. In other words, embodiments of the present invention can be used to reprogram implantable cardiac devices that are already "in the field".

Generally, FIG. 4 is used to describe methods for use by a non-implanted system configured to communicate with an implantable cardiac device implanted within a patient, wherein the implantable cardiac device is configured to detect potential episodes of tachycardia and to store data corresponding to the detected potential episodes of tachycardia, and wherein the implantable cardiac device has discriminators that the device can use to discriminate between different types of arrhythmias. Such different types of arrhythmias can include, but are not limited to, VT and SVT.

In the flow diagram of FIG. 4 (and the flow diagram of FIG. 8) the various algorithmic steps are summarized in individual "blocks" or "steps". Such blocks describe specific actions or determinations that are made or carried out as the algorithm proceeds. Where a microcontroller (or equivalent) is employed, the flow charts presented herein provide the basis for a "control program" that may be used by such a microcontroller (or equivalent) to effectuate the desired control of an implantable device and/or a non-implanted device/system. Those skilled in the art may readily write such a control program based on the flow charts and other descriptions presented herein. As will be appreciated from the discussion below, the phrase "based on", unless stated otherwise, means based at least in part on, meaning that when a determination is "based on" a factor, other factors can also be used in making the determination.

Referring to FIG. 4, at step 402, an implantable cardiac device obtains one or more EGM and/or ECG signal indicative of electrical activity of the patient's heart. Exemplary details of how step 402 can be performed are described above with reference to FIGS. 1 and 2. For example, exemplary leads, electrodes and circuits that can be used to obtain an EGM and/or ECG signal(s) were discussed above with reference to FIGS. 1 and 2. If the implantable cardiac device is a multi-chamber device, an EGM signal can be obtained for each chamber. It is well know how to obtain EGM and ECG signals, thus additional details of how to obtain such signals are not necessary.

At step 404, potential episodes of tachycardia are detected by the implantable cardiac device, based on the one or more EGM and/or ECG signal obtained at step 402. The term "potential" is used here to explain that in some instances the implantable device may incorrectly interpret a portion of an EGM/ECG as corresponding to a tachycardia. In other words, the implantable cardiac device may make an incorrect device diagnosis. An exemplary arrhythmia detector 262 that can be used to detect potential episodes of tachycardia and to make device diagnoses was described above with reference to FIG. 2. For example, measures of heart rate, RR intervals, PP intervals, etc., measured based on the obtained EGM and/or ECG signal(s) can be used to detect potential episodes of tachycardia, e.g., by comparing such measurement(s) to threshold(s).

At step 404, the implantable cardiac device can also perform arrhythmia discrimination, e.g., to classify the detected potential episode of tachycardia as either VT or SVT. More specifically, discriminators can be used to discriminate between different types of tachycardias (e.g., VT and SVT). It is well known that implantable cardiac devices can use discriminators to discriminate between different types of arrhythmias. Nevertheless, some additional details of how this can be done are provided further below.

At step 406, the implantable cardiac device stores (e.g., within memory 294) data corresponding to the detected potential episodes of tachycardia. The data stored at step 406 can include data indicative of the EGM and/or ECG signal(s) during the detected potential episodes of tachycardia. While EGM/ECG signal data for as few as one cardiac cycle can be saved at step 406, it is preferred that multiple cardiac cycles be saved for each potential episode of tachycardia, which can include normal sinus cycles occurring prior to the potential tachycardia and/or following the potential tachycardia. It is well known how to store such data so that the data can be uploaded to an external system (e.g., a programmer) at a later time.

At steps 402, physiologic information can also be obtained from one or more physiologic sensor (e.g., 208). Accordingly, physiologic data obtained from such sensors can also be stored at step 406 for detecting potential episodes of tachycardia. It is also possible that at step 404 the implantable cardiac device use the physiologic data obtained at step 402 to assist in detection of potential episodes of tachycardia and/or to assist in arrhythmia discrimination.

At steps 408 and 412, the stored data corresponding to the detected potential episodes of tachycardia, are transferred from the implantable cardiac device to the non-implanted system. More specifically, at step 408 the implantable cardiac devices sends stored data corresponding to the detected potential episodes of tachycardia, and at step 412 the non-implanted system receives such data. For example, referring back to FIG. 2, the telemetry circuit 201 and the communication link 205 can be used for the transfer of such data. The implantable device or the non-implanted system can initiate the transfer of the data, e.g., using a hand-shake protocol.

At step 414 a representation of the data (corresponding to the detected potential episodes of tachycardia) is displayed. For example, a display (e.g., 314) of a programmer (e.g., 202) can be used to graphically display a portion of an EGM and/or ECG signal waveform that corresponds to each detected potential episode of tachycardia. While as few as one cardiac cycle can be displayed for each potential episode of tachycardia, it is preferred that multiple cardiac cycles be displayed for each potential episode. It is also possible to display EGM/ECG signal waveforms of normal sinus rhythms preceding and/or following potential episodes of tachycardia so that the user can observe changes to the EGM/ECG waveforms, which may assist in the user diagnoses.

Alternatively or additionally, event markers and/or attributes of a portion of an EGM and/or ECG signal (that corresponds to each detected potential episode of tachycardia) can be displayed. Exemplary event markers that can be displayed include, e.g., P-wave marker, R-wave marker, T-wave marker, etc. Exemplary attributes that can be displayed include, e.g., RR intervals, PP intervals, PR intervals, R-wave amplitudes, P-wave amplitudes, T-wave amplitudes, etc. These are just a few examples, which are not meant to be limiting.

Figure 5A:
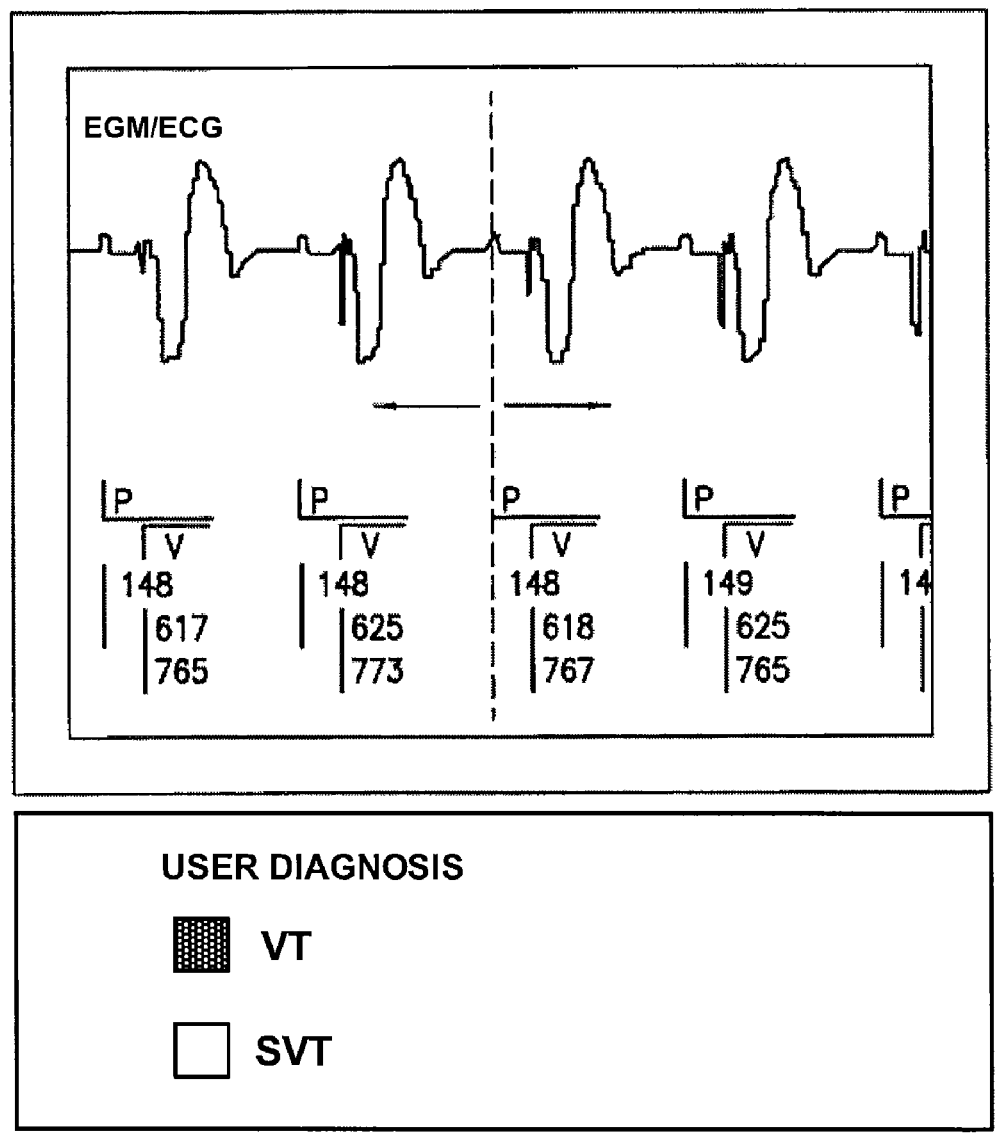
FIGS. 5A and 5B are examples of the information that can be displayed to a user for detected potential episodes of tachycardia, at one of the steps of FIG. 4, to thereby enable the user to make a user diagnosis.
Figure 5B:
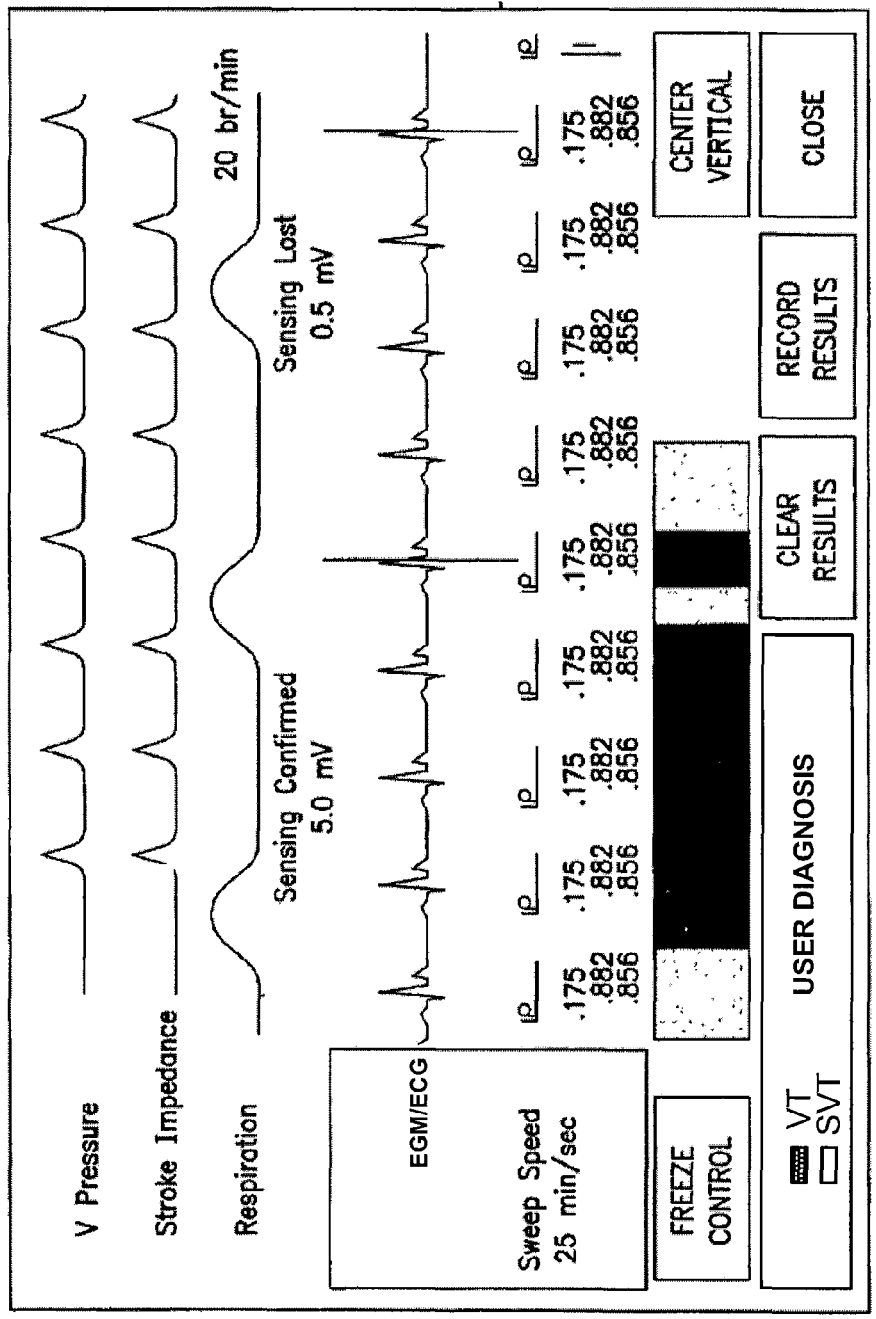

FIG. 5A illustrates an exemplary representation of data corresponding to a detected potential episode of tachycardia that can be displayed to a user. FIG. 5B illustrates another exemplary representation of data corresponding to a detected potential episodes of tachycardia that can be displayed to a user. As shown in FIG. 5B, in addition to EGM/ECG waveforms, information obtained from physiologic sensors can also be displayed to assist the user in making a diagnosis. Information about one potential detected episode of tachycardia can be displayed at one time, or information about multiple potential episodes of tachycardia can be displayed at one time.

The following patents, each of which are incorporated herein by reference, describe exemplary ways in which EGM/ECG data can be displayed to a user after it has been uploaded from an implantable cardiac device: U.S. Pat. No. 6,266,555 (Mouchawar et al.) entitled "Display for and Method of Displaying Electrograms Received from an Implantable Cardiac Stimulation Device"; U.S. Pat. No. 7,308,311 (Sorensen et al.), entitled "Physician Programmer System with Telemetered Sensor Waveform"; U.S. Pat. No. 5,697,959 (Poore), entitled "Method and System for Analyzing and Displaying Complex Pacing Event Records"; and U.S. Pat. No. 6,266,555 (Werner et al.), entitled "Single Complex Electrogram display Having a Sensing Threshold for an Implantable Medical Device." Additionally, the device diagnoses can be displayed, as can the details regarding discriminators that were used by the device to produce the device diagnoses. For example, if a morphology discriminator was turned on, then morphology match scores and device diagnoses could also be displayed. These are just examples, that are not meant to be limiting, as there are numerous alternative ways in which such data can be displayed to a user, and numerous types of additional information that can be displayed to the user.

At step 416, a user (e.g., clinician, physician, etc.) that observes the displayed representation of the data is allowed to enter a user diagnosis for each of the detected potential episodes of tachycardia (and such user diagnosis is accepted and preferably stored). This can be accomplished in various manners. For example, in a simple embodiment, the user is provided only with VT and SVT diagnosis options, as shown in FIGS. 5A and 5B. In one embodiment, if the user selects a SVT diagnosis, further options can be presented to the user including, but not limited to, atrial tachycardia (AT), atrial fibrillation (AF), atrio-ventricular nodal reentrant tachycardia (AVNRT) and SVT with bypass, thereby enabling the user to make a more specific SVT diagnosis. Similarly, if the user selects a VT diagnosis, further options can be presented to the user, including, but not limited to, monomorphic VT and polymorphic VT. The user can select one of the diagnosis options, e.g., using a touch screen (e.g., 316), keyboard (e.g., 318) or some other pointing device, such as but not limited to a mouse, touchpad, joystick, trackball, etc., or the user can type in a diagnosis. FIG. 5B illustrates that data collected from the physiologic sensor(s) 208 can also be displayed to the user to aid in the user's diagnosis. The physiologic data shown in FIG. 5B includes ventricular pressure, stroke impedance and respiration. Additional examples of types of physiologic data that can be displayed to the user were provided above.

Returning to the flow diagram of FIG. 4, at step 418, the non-implanted system simulates how the implantable cardiac device can use its discriminators to produce device diagnoses, based on the data for the detected episodes of tachycardia (i.e., based on the data transferred from the implantable cardiac device to the non-implanted system at steps 408 and 412). This can include simulating how adjustments to the discriminators affect how the device diagnoses match the user diagnoses.

It can be a programmer (e.g., similar to programmer 202) that performs the simulations. Alternatively, or additionally, some other external device, e.g., which may be in communications with a programmer, can perform the simulations. For such simulations to occur, the programmer and/or other external device (e.g., a computer system) should have knowledge of the discriminators that the implantable cardiac device is capable of using to perform arrhythmia discrimination, and how such discriminators are capable of being adjusted. For example, in an embodiment, the non-implanted system should know what discriminators the implantable device can use, how such discriminators can be used, the range of parameter values of such discriminators, the default (i.e., nominal) parameter values and uses of the discriminators, and preferably also the current programming of the discriminators (i.e., the discriminators as they are currently defined/used by the implantable device). In accordance with a specific embodiment, the user can choose which discriminators (of all possible discriminators) should be used, and the simulations can be limited to the user specified discriminators.

The implantable cardiac device (e.g., 110) can use software modules to implement portions of the algorithms related to arrhythmia discrimination. The programmer and/or other external device (and more generally, the non-implanted system) can simulate the operation of the implantable cardiac device by modeling a control unit in software, and taking into account algorithms that are implemented by a microprocessor of the implantable cardiac device. In an embodiment, the non-implanted system uses default discriminators to perform an initial simulation. In another embodiment, if at least some of the discriminators of the implantable device have already been adjusted (i.e., changed from the defaults), the non-implanted system performs an initial simulation using the discriminators as they are currently defined/used by the implantable device. The non-implanted system can upload information about an implantable devices discriminators using telemetry, as was described above, e.g., along with the data transferred at steps 408 and 412, or at another time. If the non-implanted system uploads device diagnoses from the implantable device, then the non-implanted system need not perform a simulation using the discriminators as they are currently defined/used by the implantable device, but rather, can begin by simulating adjustments to the discriminators as they are currently defined/used by the implantable device.

In accordance with an embodiment, step 418 includes making automatic adjustment(s) to one or more discriminators to thereby cause the simulated device diagnoses to more closely match that user diagnoses. This can include automatically adjusting a value of a parameter of at least one the discriminators and/or how at least one of the discriminators is used. For example, step 418 can include automatically adjusting how many discriminators must be satisfied for a rhythm to be characterized as VT, automatically adjusting which discriminators are used, automatically adjusting when discriminators are used, and/or automatically adjusting an order in which discriminators are used. Examples of discriminators that can be adjusted include, but are not limited to, a tachycardia detection rate parameter, an interval stability parameter, a sudden onset parameter, and a morphology parameter. Each of these exemplary discriminators are explained below. Values of discriminator parameters can either be increased or decreased to cause the simulated device diagnoses to more closely match that user diagnoses. Whether a value needs to be increased or decreased can depend on, e.g., the specific discriminator, the patient, and how the discriminator is used in an algorithm.

Step 418 can involve adjusting whether discriminators are turned on or off (i.e., used or not). For example, if an interval stability discriminator is turned on, then the interval stability parameter value is used in an algorithm to assist in classifying an arrhythmia as VT or SVT. In contrast, if the interval stability discriminator is turned off, then the interval stability parameter value is not used in an algorithm for such classification of an arrhythmia. Such discriminators can be, e.g., a branch of an algorithm, which can be turned on or off. In other words, adjustments to discriminators can include turning on or off branches of an algorithm.

Additionally, or alternatively, step 418 can involve adjusting how many discriminators must be satisfied for a rhythm to be characterized as VT. For example, this can include adjusting the number N, where N out of M different discriminator criteria must be satisfied for a rhythm to be characterized as VT. Additionally, or alternatively, step 418 can involve adjusting whether discriminator criteria are "AND-ed" or "OR-ed" in an algorithm. Additionally, or alternatively, step 418 can involve adjusting the order in which discriminators are used. For example, conventionally a patient's heart rate (HR) is initially compared to a tachycardia rate detection parameter, and only after the HR exceeds the tachycardia rate detection parameter is a morphology discriminator used. In other words, the primary discriminator conventionally relates to a tachycardia rate detection parameter. In accordance with an embodiment of the present invention, simulations can be performed that use a morphology discriminator (or some other discriminator) prior to a tachycardia rate discriminator, so that there can be a determination of whether changing the order of uses of discriminators causes the simulated device diagnoses to more closely match that user diagnoses. In this manner, embodiments of the present invention can be used to adjust the primary discriminator. One of ordinary skill in the art reading this description will understand that there are other possible adjustments that can be made that are also within the scope of the present invention.

For the sake of this discussion, arrhythmia discrimination can be considered optimized when the device diagnosis matches the user diagnosis, and there is as much allowance for error as possible. While a goal can be to optimize arrhythmia discrimination, embodiments of the present invention cover less than optimal improvements in arrhythmia discrimination, since absolute optimization is not always possible or practical. In accordance with an embodiment, discriminator(s) are adjusted at step 418 until the simulated device diagnoses match the user diagnoses to within a specified tolerance. There are numerous ways in which discriminators can be adjusted, examples of which are discussed below with reference to FIGS. 7A and 7B, and the flow diagram of FIG. 8. However, alternative techniques for adjustments are within the scope of the present invention.

Step 418 can result in a preferred set of discriminators. Information about the preferred discriminators and/or adjustments to currently programmed device settings can be displayed to the user at step 420, thereby enabling the user to confirm (or not confirm) that adjustments should be made. In an embodiment, the user can accept certain adjustments and reject others, or accept all adjustments.

At step 422 instructions are sent to the implantable cardiac device, specifying adjustments to the discriminators that should cause future device diagnoses produced by the implantable device to more closely match diagnoses that would be produced by the user. This can include specifying whether specific discriminator parameters should be increased or decreased in value and to what extent, or new replacement values can be provided. Changes to uses of specific discriminators can also be provided. At step 432, the implantable cardiac device receives and follows the instructions to adjust its discriminator(s). In other words, at steps 422 and 432 the implantable cardiac device is reprogrammed to adjust its discriminators. In an embodiment, step 420 is skipped, and a preferred set of discriminators determined at step 418 is used to automatically reprogram the implantable cardiac device at steps 422 and 432.

In summary, steps 412-422 in FIG. 4 could be invoked after an implantable device has collected EGM and/or ECG data at steps 402-406 with instances of arrhythmias such as SVT or VT, and preferably both. Thereafter, remotely or when a patient comes into a clinic or other medical facility, the collected data can be uploaded from the implantable device to a programmer or other external device at steps 408 and 412, and a user (e.g., qualified clinician) can visually determine a diagnosis (referred to as a user diagnosis) for the stored arrhythmias (e.g., SVT and/or VT) at step 414. The user can then enter his/her diagnosis into the system at step 416. At step 418 the non-implanted system can simulate how the implanted device can use its discriminators to perform arrhythmia discrimination, which can include discriminating VT from SVT, or can include more precise characterizations, including but not limited to atrial tachycardia (AT), atrial fibrillation (AF), atrio-ventricular nodal reentrant tachycardia (AVNRT), SVT with bypass, or monomorphic vs. polymorphic VT, etc. At step 418, the non-implanted system simulates how discriminators can be adjusted so that device diagnoses will more closely match user diagnoses.

In an embodiment, the non-implanted system can automatically cycle through all possible programming settings for all the discriminators and calculate the performance of each configuration with respect to correctly diagnosing the rhythm. Alternatively, the non-implanted system may cycle only through those discriminators that are chosen by the user. Another alternative that can increase algorithm efficiency is to start with the nominal settings or settings that are currently programmed in the device for all or the chosen discriminators and cycle through adjacent parameter values until an acceptable level of error is reached for one or more settings. The non-implanted system can then suggest and/or reprogram the implantable cardiac device settings to those that diagnosed the rhythm(s) correctly (or at least most correctly), and in an embodiment, with the greatest allowance for error. The discriminators can be adjusted in this manner from time to time, e.g., when the patient visits a medical facility, or during a remote follow-up, to adapt to changing patient conditions.

As mentioned above, most current implantable cardiac devices have the capability of storing EGM and/or ECG data corresponding to episodes of an arrhythmia. There are many triggers for EGM/ECG data storage, but they usually include an occurrence of what the device interprets as an SVT and/or VT. To increase the chances of storing SVT episodes, the device can have a "passive" zone with a low cut-off rate. If desired, to ensure that data for episodes of SVT and/or VT are stored for later uploading to the non-implanted system, VT and/or SVT can optionally be induced or simulated by the implantable device, e.g., if intrinsic occurrences of one or both are not detected.

Figure 6A:
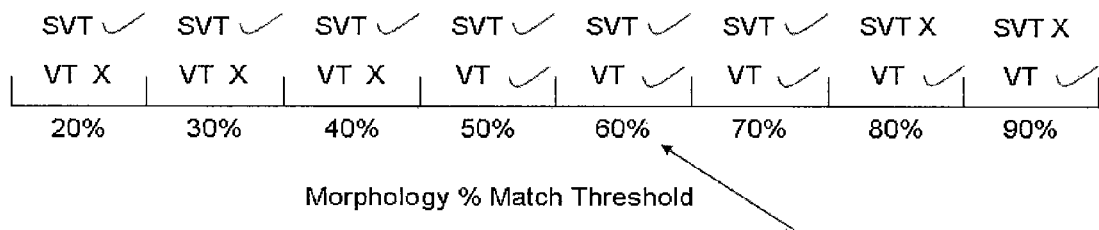
FIGS. 6A and 6B are used to describe how embodiments of the present invention can be used to select a value for a discriminator parameter that is used to discriminate between SVT and VT.

In one simple example, illustrated with reference to FIG. 6A, there is discrimination between VT and SVT, and only one discriminator is adjusted—in this case morphology score threshold. In FIG. 6A, and similar FIGS., a check mark means that the simulated device diagnosis and the user diagnosis matched, and an X means that the simulated device diagnosis and the user diagnosis did not match. For example, referring to FIG. 6A, when the morphology score threshold was set at 20%, 30% or 40%, the simulated device diagnosis for SVT matched the user diagnosis, but the simulated device diagnosis for VT did not match the user diagnosis. When a simulated device diagnosis matches a user diagnosis, it is presumed that the simulated device diagnosis is correct. When a simulated device diagnosis does not match a user diagnosis, it is presumed that the simulated device diagnosis is incorrect.

In one embodiment, at step 418 the non-implanted system can perform simulations and cycle through all the possible morphology score thresholds (e.g., 20% through 90%, at 10% increments) to determine for which threshold percentage(s) VT and SVT would be diagnosed correctly by the implantable cardiac device. In the example in FIG. 6A, when the thresholds are 20%, 30%, and 40%, SVT is diagnosed correctly, but VT is incorrect. For thresholds 80% and 90%, the opposite is true, VT is diagnosed correctly, but SVT is not. For thresholds 50%, 60%, and 70%, both SVT and VT are diagnosed correctly. In accordance with an embodiment, the discriminator parameter value with the greatest allowance for error for both VT and SVT can be chosen, which is 60% in this example. In a more efficient implementation, the simulation can start testing the thresholds at the nominal value, which can be, e.g., 60%. Use of discriminator values on either side of the nominal value can thereafter be simulated, e.g., 50% and 70%. If these both produce correct diagnoses, the simulation can go on to 40% and 80%. If these produce incorrect diagnoses, the algorithm will not test the rest of the values and can select the one out of those that produced correct diagnosis with the greatest allowance for error, the value closest to the default, or the value closest to the currently programmed device setting. Such testing can include the performance of device simulations and comparing resulting simulated device diagnoses to user diagnoses, to determine which discriminator parameter values produce correct and incorrect diagnoses.

Figure 6B:
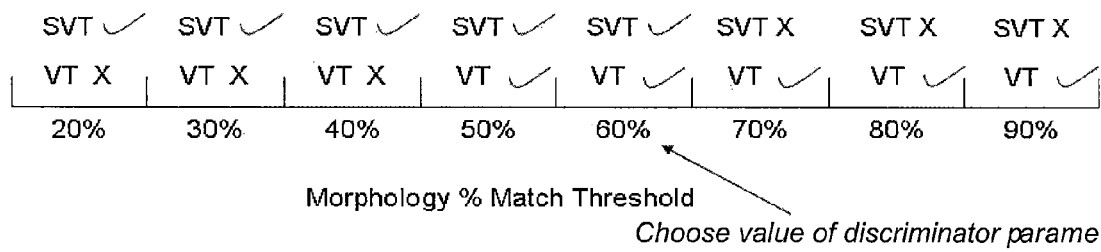

In the example in FIG. 6B, SVT and VT are diagnosed correctly only for thresholds 50% and 60%, which both have the same allowance for error. Here, the threshold closest to the device default can be chosen, e.g., 60%. Of course, this is a very simple example and most devices contain more than one discriminator that can be changed.

In another example, illustrated in FIG. 7A, there are two discriminators that can be changed, including morphology score threshold and number of morphology matches in a given window. In this case, the non-implanted system could cycle through all possible combinations of threshold and number of matches and perform simulations for each detected potential episode of tachycardia. It would then find those combinations which produce a correct diagnosis for both VT and SVT. Out of all the combinations that produce correct diagnoses, the combination with the greatest allowance for error, the closest to nominals, or the closest to the currently programmed device settings can be chosen, in accordance with embodiments. In FIG. 7A, the combination of 60% and 6/8 could be chosen because this combination correctly identifies VT and SVT and has the greatest allowance for error. In FIG. 7B, the combination of 60% and 6/8 could be chosen even though this combination has the same allowance for error as 70% and 6/8, assuming 60% is (or is closest to) the default value in the implantable device.

In a more efficient version of the algorithm, in FIG. 7A, the non-implanted system could start testing at nominal values, e.g., 60% and 5/8. All parameters can be held at nominal except one, which can be incremented and decremented. In this example, the system could try combinations 50% and 5/8, then 70% and 5/8. Since these produce correct results, the system can then try 40% and 5/8, then 80% and 5/8. These produce incorrect results, so the system would keep 50%, 60%, and 70% for the first parameter and start testing the next parameter, but only with the chosen values for the first parameter. The system could then test 60% and 5/8, 60% and 4/8, and 60% and 6/8. Since 60% and 4/8 produces a wrong diagnosis, the system would not go on in this direction, but would continue with 60% and 7/8 and then 60% and 8/8. The same logic could be followed for 50% and 70%. The system could then have a set of all the combinations that produced the correct diagnosis and choose the one with the greatest allowance for error, the one closest to the nominal values, or the one closest to the currently programmed device settings.

Figure 8:
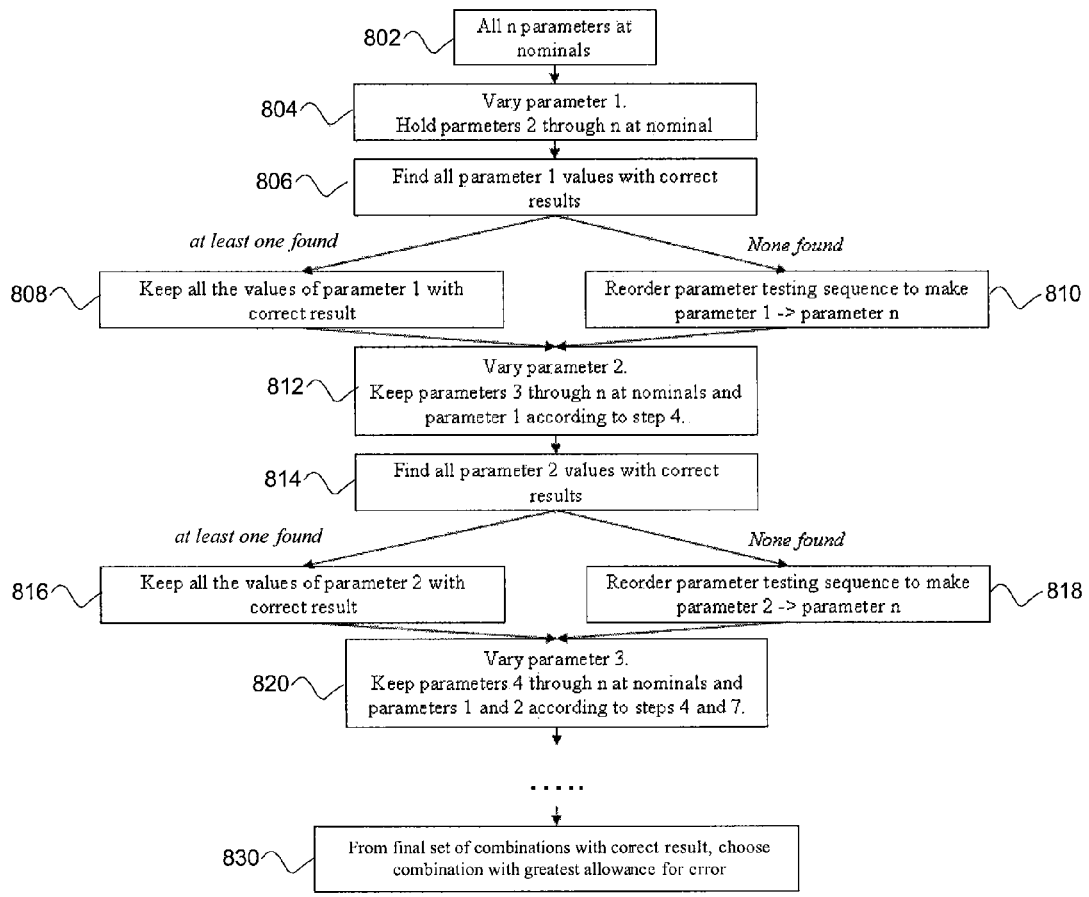
FIG. 8 is a high level flow diagram that is used to summarize how numerous discriminator parameters can be adjusted, in accordance with specific embodiments of the present invention.

Similar logic can be followed for more discriminators, including for more than one parameter of a discriminator, as illustrated in the flowchart in FIG. 8. Referring to FIG. 8, at steps 802, 804 and 806 a first parameter could be tested while keeping the rest of the parameters at nominals (i.e., defaults) or currently programmed values. Then, keeping all of the values for the first parameter that produced correct results, the second parameter can be varied, while keeping the rest of the parameters at nominal (or currently programmed values), at steps 812 and 814. If none of the combinations of the first parameter with the rest of the parameters at nominals (or currently programmed values) worked, the first parameter can be placed at the end of the parameters to be tested and the process can be repeated with the second parameter, as indicated at 810. Then the third parameter can be tested using all the values that worked for the first two parameters and the rest at nominals (or currently programmed values), as indicated at 820. Once all of the parameters have been tested, a combination can be chosen from the set that produced correct diagnosis, as indicated at 830. For example, the combination with the greatest overall allowance for error can be chosen.

The above cases are only examples and the algorithm could be implemented in a different fashion. For example, a different rule could be used to choose between combinations that produce a correct diagnosis. For example, the algorithm could choose those settings that are closest to nominals, or closest to currently programmed settings.

If for a given patient the data transferred from the implantable device to the non-implanted system corresponds to only certain types of arrhythmias (e.g., SVT but not VT), then only the arrhythmias that are available could be tested and the combination of discriminator settings should be chosen that would correctly identify the rhythm. For the case where only VT or only SVT data is available, it may be better not to choose the combination with the greatest allowance for error because such a combination may not do well with the other rhythm. So, in that instance, the combination with the greatest number of discriminators closest to defaults may be chosen, in an embodiment. Thereafter (e.g., during a later visit to a medical facility, or the like), if the data transferred from the implantable device to the non-implanted system corresponds to one or more additional type of arrhythmia (e.g., both SVT and VT), the further arrhythmia(s) that is/are available could be tested, which may provide for an even better combination of discriminator settings.

Programming of discriminations can include a simple "discriminators on/off" control (i.e., using or not using specific discriminators) and/or the ability to individually fine-tune values of parameters of discriminators such as sudden onset, interval stability, morphology discrimination, AV association threshold, etc. More specifically, the values of individual parameters of discriminators can be fine-tuned, and the combination and relationship of the various discriminators can be altered. For example, in order for the device to characterize a rhythm as VT, the user can choose to allow either morphology or interval stability criteria to be met; alternatively, the user could specify that both morphology and interval stability criteria must be met. As mentioned above, exemplary discriminators whose parameter values or uses can be adjusted include a tachycardia detection rate parameter, an interval stability parameter, a sudden onset parameter, and morphology parameters. Each of these exemplary parameters shall now be briefly discussed.

A tachycardia rate detection parameter can define the ventricular rate threshold above which a ventricular rate will be classified as a tachyarrhythmia. If no other discrimination criteria are turned on, the device will classify any rhythm with a ventricular rate above the tachycardia detection rate (but below the VF detection threshold) as a VT. This will result in a high sensitivity, but a relatively low specificity, because many SVTs may be classified as VT such as AF with fast ventricular conduction or ST during normal exercise. In order to increase the specificity, which typically results in some reduction in sensitivity, additional discriminator criteria can be turned on, and "AND-ed" with the tachycardia detection rate discriminator criteria.

An interval stability discriminator can be used to discriminate between episodes of VT and episodes of AF, because VTs are typically very stable, whereas the rhythm from one beat to the next during AF is typically less stable (i.e., more irregular). Depending upon the algorithm used, the value of an interval stability parameter can be a value of stability (also referred to as variability), which can be defined by a range, variance, standard deviation, or the like. For example, a cardiac rhythm exceeds the tachycardia detection rate parameter, and the stability is within that defined by the stability discriminator value (e.g., the standard deviation of the rhythm is less than the standard deviation discriminator value), then the arrhythmia will be classified as VT. Interval stability is sometime referred to as rate stability, because rate and interval are simply inverses of one another.

A sudden onset discriminator can help distinguish between VT and a sinus tachycardia type SVT that can be due to exercise (e.g., walking up a flight of stairs). Typically, a sinus tachycardia has a gradual rate of onset, while VT has a more abrupt onset. Such onset can be measured, e.g., by determining a difference between the average RR interval for N beats prior to a first beat that exceeds the tachycardia detection rate, and the average RR interval for N beats following the first beat that exceeds the tachycardia detection rate (e.g., N can be 1 or more). Accordingly, the value of a sudden onset discriminator parameter can be specified in milliseconds. Where the sudden onset discriminator value is exceeded, the implantable cardiac device interprets that as an indicator of VT. Where a sudden onset discriminator value is not exceeded, the implantable cardiac device interprets that as an indicator of SVT. This is just one example of a sudden onset discriminator criteria, which is not meant to be limiting.

Where both a tachycardia detection rate criteria and a sudden onset criteria are turned on (i.e., when both a tachycardia detection rate parameter and a sudden onset parameter are used), it can be that both have to be satisfied for an arrhythmia to be classified as VT. For example, if the tachycardia detection rate parameter is exceeded, but the sudden onset parameter is not exceeded, then a tachycardia may be classified as SVT. While a sudden onset discriminator parameter can be used to discriminate VT from sinus tachycardia, it can not necessarily help distinguish from other types of SVTs. As just explained above, interval stability discriminator parameter can be used to discriminate VT from AF, which conducts irregularly to the ventricles, but not necessarily discriminate from other SVTs.

As mentioned above, one or more morphology discriminator parameter can be used (e.g., a morphology discriminator criteria can be turned on). SVTs originate in the atria and follow the normal conduction pathway to the ventricles (typically via the AV node), causing the morphology (shape) of the resulting QRS complexes to look similar to the morphology of a QRS complex of a normal sinus rhythm. In contrast, VT arises from outside normal conduction pathways, causing the morphology of the resulting QRS complex to be less similar to that of a normal sinus rhythm. To perform such morphology comparisons, a template QRS complex can be obtained and stored when a patient is known to have a normal sinus rhythm. Thereafter, the template QRS complex can be compared to present QRS complexes in real or near real time, to determine a level of similarity. A morphology discriminator parameter can specify, e.g., the level of similarity (e.g., morphology score threshold) below which a rhythm is classified as indicative of VT, and above which the rhythm is classified as indicative of SVT. For a more specific example, a morphology algorithm can measure attributes such as the number of peaks, amplitude of peaks, polarity, and area under curves of a QRS complex, and compares such complexes to the template QRS complex to generate a percent match between 0 and 100%. For this example, the morphology discriminator parameter can specify the percentage match, above which a complex is classified as indicative of SVT, and below which the complex is classified as indicative of VT.

Provided above are just a few examples of discriminators that can be automatically adjusted using embodiments of the present invention. Automatic adjustments of alternative and additional discriminators (including parameters of such alternative and additional discriminators) are also within the scope of the present invention, including, but not limited to, rate branch discriminators. For example, embodiments of the present invention can be used to automatically turn on or off a rate branch algorithm, or to adjust parameters used in such an algorithm, or to turn on or off specific branches of such an algorithm.

Embodiments of the present invention, as explained above, can be used to improve arrhythmia discrimination algorithms through adjustments to discriminators employed by discrimination algorithms. Accordingly, it is believed that embodiments of the present invention can be used to improve various existing arrhythmia discrimination algorithms, including, but not limited to, Guidant's Vector Timing and Correlation (VTC) algorithm, Guidant's Rhythm ID™ algorithm, Medtronic's Wavelet™ Dynamic Discrimination algorithm, Medtronic's Enhanced PR Logic™ algorithm and Biotronik's SMART Detection™ algorithm. It is also believed that embodiments of the present invention can be used to improve future developed arrhythmia discrimination algorithms, including uses of future developed discriminators.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use by a non-implanted system configured to communicate with an implantable cardiac device implanted within a patient, wherein the implantable cardiac device is configured to detect potential episodes of tachycardia and to store data corresponding to the detected potential episodes of tachycardia, and wherein the implantable cardiac device has programmable arrhythmia discriminators and corresponding discriminator settings that the device uses to discriminate between different types of tachycardia, the method comprising:
 (a) receiving, from the implantable cardiac device implanted within the patient, data corresponding to detected potential episodes of tachycardia;
 (b) displaying a representation of the data corresponding to the detected potential episodes of tachycardia;
 (c) accepting a user diagnosis for each of the detected potential episodes of tachycardia;
 (d) simulating the implantable cardiac device's use of the discriminator settings to produce device diagnoses based on the data for the detected potential episodes of tachycardia, and repeating step (d) a plurality of times, wherein between each successive iteration of step (d) one or more of the discriminator settings is automatically adjusted, and wherein a result of each iteration of step (d) comprises a simulated device diagnosis for each of the detected potential episodes of tachycardia;

(e) comparing the simulated device diagnoses produced during multiple iterations of step (d) to the user diagnoses accepted at step (c) to thereby identify discriminator settings, and/or adjustments to currently programmed discriminator settings, that cause the device diagnoses to more closely match the user diagnoses; and (f) displaying information about the identified discriminator settings, and/or adjustments to currently programmed discriminator settings, that cause the device diagnoses to more closely match the user diagnoses;

wherein each of steps (a), (b) and (c) occur prior to each of steps (d), (e) and (f); and wherein at step (e), if a plurality of different settings for a specific one of the discriminators results in the same match between the simulated device diagnoses and the user diagnoses, then selecting one of the plurality of different settings for the specific one of the discriminators based on:

which one of the different settings for the specific one of the discriminators provides the greatest allowance for error;

which one of the different settings for the specific one of the discriminators is the same as or closest to a corresponding default setting of the implantable cardiac device; and/or which one of the different settings for the specific one of the discriminators is the same as or closest to a corresponding currently programmed setting of the implantable cardiac device.

2. The method of claim 1, wherein step (d) includes automatically adjusting one or more of the discriminator settings until results of the comparing at step (e) indicate that the simulated device diagnoses match the user diagnoses to within a specified tolerance.

3. The method of claim 1, further comprising:

(g) sending instructions to the implantable cardiac device, the instructions specifying the identified discriminator settings and/or adjustments to currently programmed discriminator settings that cause the device diagnoses to more closely match the user diagnoses.

4. The method of claim 1, wherein step (d) includes automatically adjusting one or more of the following settings:

which discriminators are used;
when discriminators are used;
how discriminators are used;
an order in which discriminators are used;
how many discriminators must be satisfied for a rhythm to be characterized as a specific type of tachycardia; and
a value of a parameter of at least one of the discriminators.

5. The method of claim 1, wherein at step (e), if more than one setting for one of the discriminators results in the same match between the simulated device diagnoses and the user diagnoses, then selecting the setting that provides the greatest allowance for error.

6. The method of claim 5, wherein at step (e), if more than one setting for one of the discriminators results in the same match between the simulated device diagnoses and the user diagnoses, and results in the same allowance for error, then selecting the setting that is the same as or closest to a corresponding default setting of the implantable cardiac device.

7. The method of claim 1, wherein at step (e), if more than one setting for one of the discriminators results in the same match between the simulated device diagnoses and the user diagnoses, then selecting the setting that is the same as or closest to a corresponding default setting of the implantable cardiac device.

8. The method of claim 1, wherein at step (e), if more than one setting for one of the discriminators results in the same match between the simulated device diagnoses and the user diagnoses, then selecting the setting that is the same as or closest to a corresponding currently programmed setting of the implantable cardiac device.

9. The method of claim 1, wherein step (b) includes displaying EGM and/or ECG waveforms corresponding to the detected potential episodes of tachycardia.

10. The method of claim 9, step (b) includes displaying attribute information about the displayed EGM and/or ECG waveforms corresponding to the detected potential episodes of tachycardia.

11. The method of claim 9, wherein:

step (a) includes receiving, from the implantable cardiac device implanted within the patient, physiologic data corresponding to detected potential episodes of tachycardia, the physiologic data obtained using one or more physiologic sensor;

step (b) includes displaying, along with the EGM and/or ECG waveforms, a representation of the physiologic data that corresponds to the detected potential episodes of tachycardia.

12. The method of claim 1, wherein:

step (c) includes allowing the user to select from among at least VT and SVT user diagnosis options for each of the detected episodes of tachycardia.

13. The method of claim 1, wherein step (d) includes automatically adjusting one or more of the following settings:

an order in which discriminators are used; and
how many discriminators must be satisfied for a rhythm to be characterized as a specific type of tachycardia.

14. A non-implanted system configured to communicate with an implantable cardiac device implanted within a patient, wherein the implantable cardiac device is configured to detect potential episodes of tachycardia and to store data corresponding to the detected potential episodes of tachycardia, and wherein the implantable cardiac device has programmable arrhythmia discriminators and corresponding discriminator settings that the device uses to discriminate between different types of tachycardia, the non-implanted system comprising:

a telemetry subsystem to receive, from the implantable cardiac device implanted within the patient, data corresponding to detected potential episodes of tachycardia;

a display to display a representation of the data corresponding to the detected potential episodes of tachycardia;

an input device to accept, from a user that observes the displayed representation of the data, a user diagnosis for each of the detected potential episodes of tachycardia;

one or more processor to perform a simulation to simulate the implantable cardiac device's use of the discriminator settings to produce device diagnoses based on the data for the detected potential episodes of tachycardia, repeat the simulation a plurality of times, wherein between each successive iteration of the simulations one or more of the discriminator settings is automatically adjusted, and wherein a result of each iteration of the simulations comprises a simulated device diagnosis for each of the detected potential episodes of tachycardia, and compare the simulated device diagnoses produced during multiple iterations of the simulations to the accepted user diagnoses to thereby identify discriminator settings, and/or adjustments to currently programmed discriminator settings, that cause the device diagnoses to more closely match the user diagnoses;

wherein the display also displays information about the identified discriminator settings, and/or adjustments to currently programmed discriminator settings, that cause the device diagnoses to more closely match the user diagnoses; and wherein if a plurality of different settings for a specific one of the discriminators results in the same match between the simulated device diagnoses and the user diagnoses, then the one or more processor selects one of the plurality of different settings for the specific one of the discriminators based on:

which one of the different settings for the specific one of the discriminators provides the greatest allowance for error;

which one of the different settings for the specific one of the discriminators is the same as or closest to a corresponding default setting of the implantable cardiac device; and/or which one of the different settings for the specific one of the discriminators is the same as or closest to a corresponding currently programmed setting of the implantable cardiac device.

15. The system of claim 14, wherein the one or more processor automatically adjusts one or more of the discriminator settings until results of the comparison indicate that the simulated device diagnoses match the user diagnoses to within a specified tolerance.

16. The system of claim 14, wherein:

the telemetry subsystem also sends instructions to the implantable cardiac device, the instructions specifying the identified discriminator settings and/or adjustments to currently programmed discriminator settings that cause the device diagnoses to more closely match the user diagnoses.

17. The system of claim 14, wherein the one or more processors automatically adjust one or more of the following settings between at least some of the iterations of the simulations:

an order in which discriminators are used; and how many discriminators must be satisfied for a rhythm to be characterized as a specific type of tachycardia.

\* \* \* \* \*